(12) United States Patent
Patnaik et al.

(10) Patent No.: US 6,803,069 B2
(45) Date of Patent: Oct. 12, 2004

(54) METHOD FOR IMPARTING A BIO-ACTIVE COATING

(75) Inventors: Birendra K. Patnaik, Chester, NJ (US); Horng-Ban Lin, Randolph, NJ (US); David J. Lentz, Randpolph, NJ (US); Richard J. Zdrahala, Montville, NJ (US)

(73) Assignee: SciMed Life Systems, Inc., Maple Grove, MN (US)

( * ) Notice: Subject to any disclaimer, the term of this patent is extended or adjusted under 35 U.S.C. 154(b) by 39 days.

(21) Appl. No.: 09/885,361

(22) Filed: Jun. 20, 2001

(65) Prior Publication Data

US 2001/0044655 A1 Nov. 22, 2001

Related U.S. Application Data

(63) Continuation of application No. 08/713,800, filed on Sep. 13, 1996, now Pat. No. 6,306,165.

(51) Int. Cl.[7] ............................. B05D 3/00; B05D 3/04; A61L 27/00
(52) U.S. Cl. ...................... 427/2.24; 427/2.1; 427/2.25; 427/2.26; 427/2.27; 427/2.28; 427/2.3; 427/2.31; 427/532; 427/533; 427/535; 427/536; 427/299; 427/402; 427/407.1
(58) Field of Search ................................ 427/2.1, 2.24, 427/2.25, 2.26, 2.27, 2.28, 2.3, 2.31, 532, 533, 535, 536, 299, 402, 407.1; 623/1.1, 1.11, 2.1, 11.11, 1.42, 1.43, 6.57, 6.62, 23.71

(56) References Cited

U.S. PATENT DOCUMENTS

| | | | |
|---|---|---|---|
| 4,229,838 A | 10/1980 | Mano | |
| 4,331,697 A | 5/1982 | Kudo et al. | |
| 4,521,564 A | 6/1985 | Solomon et al. | |
| 4,600,652 A | 7/1986 | Solomon et al. | |
| 4,613,517 A | 9/1986 | Williams et al. | |
| 4,642,242 A | 2/1987 | Solomon et al. | |
| 4,678,660 A | 7/1987 | McGary et al. | |
| 4,713,402 A | 12/1987 | Solomon | |
| 4,720,512 A | 1/1988 | Hu et al. | |
| 4,786,556 A | * 11/1988 | Hu et al. | 428/412 |
| 4,973,493 A | 11/1990 | Guire | |
| 4,979,959 A | 12/1990 | Guire | |
| 5,028,597 A | 7/1991 | Kodama et al. | |
| 5,061,777 A | 10/1991 | Yoda et al. | |
| 5,077,352 A | 12/1991 | Elton | |
| 5,077,372 A | * 12/1991 | Hu et al. | 602/48 |
| 5,132,108 A | 7/1992 | Narayanan et al. | |
| 5,134,192 A | 7/1992 | Feijen et al. | |
| 5,171,264 A | 12/1992 | Merrill | |
| 5,244,654 A | * 9/1993 | Narayanan | 424/78.17 |
| 5,258,041 A | 11/1993 | Guire et al. | |
| 5,336,518 A | 8/1994 | Narayanan et al. | |
| 5,409,696 A | 4/1995 | Narayanan et al. | |
| 5,436,291 A | 7/1995 | Levy et al. | |
| 5,451,424 A | 9/1995 | Solomon et al. | |

FOREIGN PATENT DOCUMENTS

| | | |
|---|---|---|
| EP | 0 263 184 A1 | 4/1988 |
| EP | 0 404 515 A2 | 12/1990 |
| EP | 0 519 087 A1 | 12/1992 |
| EP | 0 790 042 A2 | 8/1997 |
| WO | WO 89/05616 | 6/1989 |
| WO | WO 90/00343 | 1/1990 |
| WO | WO 91/15952 | 10/1991 |
| WO | WO 91/19521 | 12/1991 |
| WO | WO 94/10938 | 5/1994 |

OTHER PUBLICATIONS

Heparin Immobilization by Surface Amplication, Ai–Zhi Piao, Harvey A. Jacobs, Ki Dong Park, and Sung Wan Kim, ASAIO Journal 1992, Slide Forum 26, Biomaterials/Surface Treatments, ppg. M638–M643.

Heparin Immobilization onto Segmented Polyurethaneurea Surfaces–Effect of Hydrophilic Spacers, by Ki Dong Park, Teruo Okano, Chisato Nojiri, and Sung Wan Kim, Journal of Biomedical Materials Research, vol. 22, 977–992 (1988).

SPUU–PEO–Heparin Graft Copolymer Surfaces, Patency and Platelet Deposition in Canine Small Diameter Arterial Grafts by Won Gon Kim Ki Dong Park, Syed F. Mohammad, and Sung Wan Kim.

Synthesis and Characterization of SPUU–PEO–Heparin Graft Copolymers, by Ki Dong Park, Al Zhi Piao, Harvey Jacobs, Teruo Okano and Sung Wan Dim, Journal of Polymer Science: Part A: Polymer Chemistry; vol. 29, 1725–1737 (1991).

PEO–Modified Surfaces–In Vitro, Ex Vivo, and In Vivo Blood Compatibility by Ki Dong Park and Sung Wan Kim Poly (Ethylene Glycol) Chemistry: Biotechnical and Biomedical Applications, 283–301 (1992).

In Vivo Nonthrombogenicity of Heparin Immobilized Polymer Surfaces by Chisato Nojiri, Ki Dong Park, David W. Grainger, Harvey A. Jacobs, Teruo Okano, Hitoshi Koyanagi, and Sung Wan Kim.

* cited by examiner

Primary Examiner—Shrive P. Beck
Assistant Examiner—Jennifer Kolb Michener
(74) Attorney, Agent, or Firm—Kenyon & Kenyon

(57) ABSTRACT

Disclosed are implantable medical devices with enhanced patency. Expanded polytetrafluoroethylene small caliber vascular grafts coated with polymer bound bio-active agents that exhibit enhanced patency are disclosed. The polymer bound bio-active agents can include anti-thrombogenic agents, antibiotics, antibacterial agents and antiviral agents. Methods of preparing same are also provided.

4 Claims, No Drawings

METHOD FOR IMPARTING A BIO-ACTIVE COATING

RELATED U.S. APPLICATION DATA

This application is a continuation of U.S. patent application Ser. No. 08/713,800 filed on Sep. 13, 1996. Now U.S. Pat. No. 6,306,165.

FIELD OF INVENTION

The present invention generally relates to implantable medical devices with enhanced patency. More particularly, the present invention relates to ePTFE small caliber vascular grafts that have significantly enhanced patency when coated with polymer bound bio-active agents and methods of applying these agents to such grafts.

BACKGROUND OF THE INVENTION

It is well known to use bio-active materials to coat structures to be introduced into a living system. Over the last 30 years, research into this area has become increasingly important with the development of various bio-compatible articles for use in contact with blood, such as, for example, vascular grafts, artificial organs, endoscopes, cannulas, and the like.

While various materials have been used to make such articles, synthetic polymers have been increasingly popular as the preferred materials due to their anti-thrombogenic and good mechanical properties. For example, polyurethane is a useful and effective material with a variety of clinical applications. Although synthetic polymers, such as, PTFE and polyurethane, are less thrombogenic than earlier materials, thrombus formation is still a problem.

A thrombus is the formation of a solid body composed of elements of the blood, e.g., platelets, fibrin, red blood cells, and leukocytes. Thrombus formation is caused by blood coagulation and platelet adhesion to, and platelet activation on, foreign substances. When this occurs, a graft is occluded by such thrombogenic material, which in turn, results in decreased patency for the graft. Accordingly, more stringent selection criteria are necessary for small caliber vascular graft materials because the small diameters of these grafts magnify the problem of deposition of such thrombogenic material on the luminal surfaces of the graft. Thus, thrombus formation is a serious complication in surgery and clinical application of small caliber vascular grafts.

Various anti-thrombogenic agents, such as heparin, have been developed and incorporated into bio-compatible articles to combat thrombus formation. In a living system, heparin inhibits the conversion of a pro-enzyme (prothrombin) to its active form (thrombin). Thrombin catalyzes a complicated biochemical cascade which ultimately leads to the formation of a thrombus.

Infection is also a serious concern for articles to be implanted into a host organism. Bacterial, viral and other forms of infection may lead to life-threatening complications when an article is implanted into a host organism. Thus, binding of an anti-infection agent to a surface of an implantable article can reduce the risk of infection when such an article is introduced into a host organism.

The art is replete with various procedures for preventing thrombus formation and/or infection by modifying polymeric surfaces. Various substrate surfaces have previously been described that are suitable for introducing into a biological system. For example, bio-compatible polymer surfaces have been described with various benefits including decreased thrombogenicity, increased abrasion-resistance and improved hydrophilic lubricious properties. Additionally, U.S. Pat. No. 5,061,777 describes procedures for modifying polyurethanes and polyurethaneureas in order to decrease their thrombogenicity. Similarly, U.S. Pat. No. 5,077,352 describes a method of forming a polyurethane complexed with a poly(ethylene oxide) having good adherence to a substrate and good anti-friction properties.

These polymer surfaces, however, are not completely bio-compatible. Thrombus formation and infection continue to pose problems when such articles are implanted within a host. These articles especially are not suitable for use with small caliber vascular grafts where graft patency is critical. Thus, procedures for grafting bio-active agents onto a substrate surface have been developed.

For example, bio-active agents directly bound to the polymer backbone of a polymer coating material are known. Hu et al. in U.S. Pat. No. 5,077,372 disclose a medical device coated with an anti-thrombogenic agent, e.g., heparin, covalently linked to the amino groups of the polyurethane coating. These coating reactions and heparinizations are carried out directly on the device's surface. Such methods, however, suffer from decreased bio-activity, and consequently, increased thrombogenicity because the bio-active agent, such as, heparin, must be positioned at a distance from the substrate surface in order to optimally interact with its physiological substrates.

Accordingly, alternative methods have been developed for binding bio-active molecules to substrate surfaces. In particular, methods for ionically binding bio-active agents to a substrate via a quarternary ammonium compound have been described. See for example, Mano in U.S. Pat. No. 4,229,838; Williams et al. in U.S. Pat. No. 4,613,517; McGary et al. in U.S. Pat. No. 4,678,660; Solomon et al. in U.S. Pat. No. 4,713,402; and Solomon et al. in U.S. Pat. No. 5,451,424.

These methods, however, are severely limited because the bio-active agent is leached over time from the surface of the substrate. Thus, the protection afforded by the ionically bound bio-active agent is transient at best. Such procedures, therefore, also are not suitable for small caliber grafts.

Accordingly, more permanent methods for binding bio-active molecules to substrate surfaces have also been developed. These methods include covalently binding a bio-active molecule, either directly, or via a spacer molecule, to a substrate surface. For example, photochemical reactions are described which covalently bind bio-active agents to substrate surfaces. See U.S. Pat. Nos. 4,331,697; 4,973,493; 4,979,959; and 5,258,041. When photochemical reactions are used to covalently bind bio-active agents to substrates, however, the choice of substrate is limited. Actinic radiation causes certain substrates, for example PTFE, to degrade. Thus, these methods are limited by the substrate material to be coated.

Even though photochemical reactions are limited to use with certain actinic radiation-resistant substrates, these reactions have been used to indirectly bind bio-active coatings to such substrates via a spacer molecule. For example, several studies describe polyurethane coatings having various spacer molecules that link bio-active agents to polymer substrates. These studies indicate that bio-active agents, such as, for example, heparin, bound to polymer coatings retain more of their bio-activity if they are tethered away from the surface of an article by a spacer.

Thus, Bichon et al. in U.S. Pat. No. 4,987,181 describe a substrate having an adhesive film with anti-thrombogenic properties on its surface. This adhesive film is an olefinic copolymer having carboxylic side chains of the formula $O=CH-NH_2-(CH_2)_n-NH_2-CH_2-R$, wherein R is a heparin molecule or a depolymerization fragment of a heparin molecule. The adhesive film is deposited onto the substrate via photo-initiated polymerization of a suitable monomer. Thus, heparin, or a fragment thereof, is covalently linked to the substrate via an amine spacer.

Although covalent bonding of the bio-active agent to the substrate surface with, or without, a spacer molecule therebetween solves certain problems in the art, these methods continue to be limited. In particular, certain bio-active coatings begin to degrade in response to the photochemical signals used to bind them to the substrate surfaces. In a similar fashion, certain polymeric substrates, such as, polytetrafluoroethylene, degrade when exposed to photochemical reactions and are therefore not useful with such coatings. Thus, attempts have been made to use spacer molecules to bind bio-active agents to substrate surfaces without photochemical reactive groups.

For example, in a four step process, Park et al. disclose immobilizing heparin onto a commercial preparation of a segmented polyetherurethaneurea (PUU) using hydrophilic poly(ethylene oxide) (PEO) spacers of different molecular weights. Their method includes (1) coupling hexamethyldiisocyanate (HMDI) to a segmented polyurethaneurea backbone through an allophanate/biuret reaction between the urethane/urea-nitrogen proton and one of the isocyanate groups on the HMDI. Next, (2) the free isocyanate groups attached to the backbone are then coupled to a terminal hydroxyl group on a PEO to form a PUU-PEO complex. Next (3) the free hydroxyl groups of the PUU-PEO complex are treated with HMDI to introduce a terminal isocyanate group. Finally, (4) the NCO functionalized PUU-PEO is then covalently bonded to reactive functional groups on heparin (—OH and —NH$_2$) producing a PUU-PEO-Hep product. K. D. Park and S. W. Kim, "PEO-Modified Surfaces—In Vitro, Ex Vivo and In Vivo Blood Compatibility", in Poly(Ethylene Glycol) Chemistry: Biotechnical and Biomedical Applications 283 (J. Milton Harris ed. 1992). This method will be referred to hereinafter as the "Park Method."

Although the use of spacer molecules to tether bio-active molecules to substrate surfaces increases the anti-thrombogenicity of certain substrate surfaces, problems still arise in applying such coatings to chemically inert substrates, such as PTFE, PET and the like. These coatings, which have hydrophilic properties adhere weakly, if at all, to hydrophobic chemically inert substrate surfaces. Thus, the natural repulsive forces between the hydrophilic coatings and the hydrophobic substrate surface serves to decrease the ability of the coating to remain secured to the substrate surface. Thus, plasma treatment of substrate surfaces has been developed as a method to alter the surface properties of such substrates in order to secure coatings thereto.

Accordingly, surfaces of chemically inert tubes have been modified in order to promote binding between a coating and the substrate surface by deposition of a thin layer of an appropriate polymer onto the substrate surface using plasma polymerization (also known as glow discharge) techniques. This technique involves introducing a polymerizable organic monomer in a gaseous state into a vacuum container together with the substrate material to be coated. The gas is then subjected to an electric discharge which initiates a polymerization reaction. This reaction generates ions or free radicals which react with and deposit on the substrate. The polymer formed is normally deposited as a thin layer over the substrate material present in the reaction vessel. Critically, the bulk substrate characteristics are preserved, but the surface properties, which are major determinants of bio-compatibility and non-thrombogenicity, can be modified or improved by plasma polymerization.

Accordingly, Hu et al. in U.S. Pat. No. 4,720,512 describe a method for imparting improved anti-thrombogenic activity to a polymeric support structure by coating it with an amine-rich material, e.g., polyurethaneurea, introducing hydrophobic groups into the amine-rich surface coating through plasma treatment with fluorine compounds, and covalently bonding an anti-thrombogenic agent to the hydrophobic amine-rich surface. Similarly, Hu et al. in U.S. Pat. No. 4,786,556 describe substituting siloxane and silazane compounds during the plasma treatment step of the '512 patent for the previously disclosed fluorine compounds. See also, Narayanan et al. in U.S. Pat. Nos. 5,132,108 and 5,409,696 and Feijen et al. in U.S. Pat. No. 5,134,192 for other examples of plasma treating substrates prior to introduction of a bio-active molecule.

These preceding methods for plasma treating a substrate surface are limited in their scope because they only work with certain substrates. Thus, they do not provide a general purpose coating composition that can bind to a variety of substrate surfaces.

All of these disclosures have addressed substrate surfaces and/or coatings therefor which can exist within biological systems and, in particular, can increase the anti-thrombogenicity of the surface of, e.g., medical articles. These reactions, however, cannot be universally applied to substrate surfaces. Accordingly, when chemically inert ePTFE vascular grafts are desired to be used, they must be implanted without the benefit of, e.g., an anti-thrombogenic coating, or with one of the previously described coatings. In either case, the patency of the graft is severely compromised because foreign bodies build up on and occlude the graft. This is especially problematic in small caliber grafts where the diameter of the lumen is smaller than other larger diameter vascular grafts. Thus, there is a need for a chemically inert vascular graft material with increased patency and methods of making such a graft. In particular, there is a need for a chemically inert small caliber vascular graft having a surface that adheres well to bio-active coatings applied thereto. The present invention is directed toward providing such a solution.

SUMMARY OF THE INVENTION

The present invention relates to implantable medical devices with enhanced patency. In particular, the present invention is directed to an implantable medical device having at least one hydrophobic surface that includes a bio-active coating bound thereto. The bio-active coating contains a polymer backbone bound via an amide or amine chemical bond to one end of a hydrophilic, amine terminated spacer that has at least one amine group at its first and second ends. A bio-active molecule is covalently bound to the unreacted end of the hydrophilic spacer. The hydrophilic spacer is repelled by the hydrophobic surface of the medical device in such a way that the bio-active molecule is extended away from the hydrophobic surface.

In the present invention, the bio-active agent further includes a polymer structure which is defined by a biocompatible polymeric backbone and at least one pendant moiety of the general formula

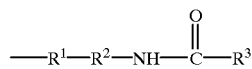

In this formula, $R^1$ is

$R^2$ is a spacer group selected from the group consisting of oxygenated polyolefins, aliphatic polyesters, polyamino acids, polyamines, hydrophilic polysiloxanes, hydrophilic polysilazanes, hydrophilic acrylates, hydrophilic methacrylates, linear and lightly branched polysaccharides. $R^3$ is a bio-active agent selected from the group consisting of antithrombogenic agents, antibiotic agents, antibacterial agents, antiviral agents, their pharmaceutical salts and mixtures thereof.

In the present invention, any medical device may be used. Preferably the medical device of the present invention is an implantable device such as a vascular graft, endoprosthesis or stent. Other medical devices may also be used, such as, catheters which are minimally invasive. The vascular graft may include a hollow tubular body having an inner and an outer hydrophobic surface. More preferably, the device of the present invention is a small caliber vascular graft and most preferably an ePTFE vascular graft. For purposes of this invention, the term "vascular graft" is meant to include endoprostheses which are generally introduce via catheter.

In another embodiment of the present invention, a medical device is provided that includes a bio-active coating over a body fluid contacting surface of the medical device for contacting body fluids. In this embodiment of the invention, the body fluid contacting surface is covalently bonded to the bio-active coating. The bio-active coating includes a polymeric structure defined by a bio-compatible polymeric backbone and at least one pendant moiety of the general formula.

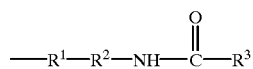

In this formula, $R^1$ is

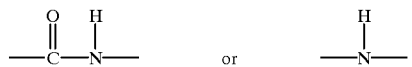

$R^2$ is a spacer group having a chain length of about 9 to about 400 atoms (approximately 100 daltons to 200,000 daltons). Preferably the spacer group has a chain length from about 60 to about 250 atoms. For example, the spacer group may include oxygenated polyolefins, aliphatic polyesters, polyamino acids, polyamines, hydrophilic polysiloxanes, hydrophilic polysilazanes, hydrophilic acrylates, hydrophilic methacrylates, linear and lightly branched polysaccharides. $R^3$ is a bio-active agent selected from the group consisting of antithrombogenic agents, antibiotics agents, antibacterial agents, antiviral agents, their pharmaceutical salts and mixtures thereof.

In yet another embodiment of the invention, there is provided a surface-modified implantable sheet material whose treated surface when exposed to a body fluid is antithrombogenic over extended periods of time. This implantable sheet material includes a hydrophobic substrate material having a plasma induced hydrophilic functionality and a bio-active coating covalently bonded thereto. The sheet can be formed into surgical mesh patches or plugs for tissue and muscle defects, such as, hernias. The bio-active coating has a polymeric structure defined by a bio-compatible polymeric backbone and at least one pendant moiety selected from the group consisting of

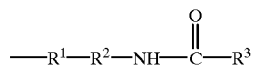

wherein $R^1$ is

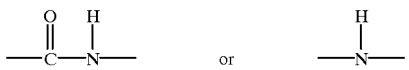

$R^2$ is a spacer group having a chain length of about 9 to about 400 atoms (approximately 100 daltons to about 200,000 daltons). Preferably the spacer group has a chain length from about 60 to about 250 atoms. For example, the spacer group may include oxygenated polyolefins, aliphatic polyesters, polyamino acids, polyamines, hydrophilic polysiloxanes, hydrophilic polysilazanes, hydrophilic acrylates, hydrophilic methacrylates, linear and lightly branched polysaccharides. $R^3$ is a bio-active agent selected from the group consisting of antithrombogenic agents, antibiotics, antibacterial agents, antiviral agents, their pharmaceutical salts and mixtures thereof.

In a further embodiment of the present invention, the medical device having at least one hydrophobic surface has a bio-active coating thereon which is the reaction product of a polymeric backbone, an amine-terminated hydrophilic spacer and a bio-active agent. This product is initiated by a first reaction that includes reacting in the presence of a first dehydrating agent a bio-compatible polymer backbone containing one or more functional groups selected from the group consisting of carboxyl functionality and mixtures thereof with a hydrophilic, amine-terminated spacer having at least one amine group at its first and second ends. In this first reaction, one of the amine groups reacts with one or more functional groups in the polymer backbone to bond the spacer to the polymer backbone. The bio-active coating includes a second reaction in which a bio-active agent is reacted with the remaining unreacted amine terminated end of the spacer in the presence of a second dehydrating agent, which may be the same or different as the first dehydrating agent, to covalently bind the bio-active agent to the spacer.

Application of the bio-active coating is by conventional methods which are known in the art. These methods include, without limitation, dipping, steeping and spraying the article with the bio-active coating. Additional coating and impregnation techniques using pressure to force the coating into the substrate interstices are also contemplated. Multiple layers of the bio-active coating may be applied to the article. Preferably, from about 1 to about 10 layers of the polymer bound bio-active agent are applied to the surface of the article.

In another embodiment of the invention the luminal surface of an article, such as an ePTFE graft, is plasma treated so that hydrophilic groups generated from a gaseous material are introduced onto the surface thereof. Any plasma treatment which is capable of introducing hydrophilic groups onto the surface of an ePTFE vascular graft is useful. It is preferred that a hydrogen-rich plasma be used. Next, the plasma treated surface is contacted with a bio-active coating. The bio-active coating is the reaction product of a first reaction that includes reacting in the presence of a first dehydrating agent a biocompatible polymer backbone containing one or more functional groups selected from the group consisting of carboxyl functionality, unsaturated functionality and mixtures thereof with a hydrophilic amine-terminated spacer having a first end and a second end. The first and second ends of the hydrophilic spacer each have an amine group wherein one of the amine groups reacts with one or more functional groups on the polymer backbone in the presence of a dehydrating agent. This method further includes a second reaction in which a bio-active agent reacts with the remaining unreacted amine-terminated end of the spacer in the presence of a second dehydrating agent to covalently bind the bio-active agent to the spacer.

In this method, the luminal surface of the ePTFE vascular graft includes nodes and fibrils that are resistant to plasma treatment. That is, plasma treatment will not degrade this structure. Conventional plasma treatment, which is known in the art, is useful in this method. For example, the plasma treatment may take place in a plasma ionization chamber with the following parameters: (a) a gas flow rate of about 1 to 500 ml/minute; (b) a chamber pressure of about 0.1 to about 100 torrs; (c) a power setting of about 1 to 700 watts; and (d) a sample exposure time of from about 1 minute to about 24 hours.

In a still further embodiment of the present invention, a method of imparting a bio-active coating to a surface of an article is provided. This method includes plasma treating a surface of the article together with a gaseous material in an ionization chamber so that hydrophilic groups generated from the gaseous material are introduced onto a surface of the article in order to provide a hydrophilic environment thereon. Then, the surface is contacted with a coating composition that includes a polymeric structure defined by a bio-compatible polymeric backbone and at least one pendant moiety selected from the group consisting of

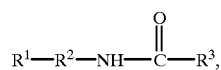

wherein $R^1$ is

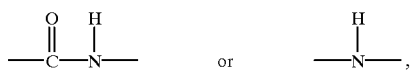

$R^2$ is a spacer group having from about 9 to about 400 atoms (approximately 100 daltons to about 200,000 daltons) and preferably from about 60 to about 250 atoms. $R^2$ is further selected from the group consisting of oxygenated polyolefins, aliphatic polyesters, polyamino acids, polyamines, hydrophilic polysiloxanes, hydrophilic polysilazanes, hydrophilic acrylates, hydrophilic methacrylates, linear and lightly branched polysaccharides. $R^3$ is a bio-active agent selected from the group consisting of antithrombogenic agents, antibiotics agents, antiviral agents, their pharmaceutical salts and mixtures thereof.

In a further embodiment of the invention, another method of imparting a bio-active coating to a surface of an article is provided. This method includes plasma treating the surface of the article together with a gaseous material in an ionization chamber so that hydrophilic groups generated from the gaseous material are introduced onto the surface of the article in order to provide a hydrophilic environment thereon. Then, the surface is contacted with a polymer bound bio-active composition represented by the structure:

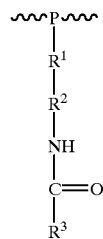

wherein P is a bio-compatible polymer selected from the group consisting of bio-compatible polymers having carboxyl functionality, unsaturated functionality, and mixtures thereof; $R^1$ is

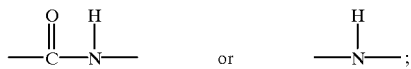

$R^2$ is a hydrophilic amine-terminated spacer selected from the group consisting of oxygenated polyolefins, aliphatic polyesters, polyamino acids, polyamines, hydrophilic polysiloxanes, hydrophilic polysilazanes, hydrophilic acrylates, hydrophilic methacrylates, linear and lightly branched polysaccharides; and $R^3$ is a bio-active agent selected from the group consisting of anti-thrombogenic agents, antibiotic agents, antibacterial agents, their pharmaceutical salts, and mixtures thereof.

The bio-active agent useful in the present invention may be chosen from a wide variety of materials. Examples include agents selected from the group consisting of anti-thrombogenic agents, antibiotic agents, antibacterial agents, antiviral agents, their pharmaceutical salts, and mixtures thereof Furthermore, the bio-active agent is selected from the group consisting of heparin, prostaglandins, urokinase, streptokinase, sulfated polysaccharide, albumin, their pharmaceutical salts and mixtures thereof.

DETAILED DESCRIPTION OF THE INVENTION

While this invention is satisfied by embodiments in many different forms, there will be described herein in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the present invention, there are provided novel plasma treated chemically inert substrates with bio-active coatings and their use in developing antithrombogenic and/or anti-infective articles. More particularly, new bio-active coatings prepared by novel reaction schemes are provided for ePTFE vascular grafts. Also provided are methods for applying heparinized polymers as antithrombogenic coatings in, e.g., small caliber ePTFE vascular grafts.

The bio-active coatings and methods described herein are particularly advantageous over previously disclosed polymer coatings because the composition and structure of the present coatings are more controllable and reproducible. In addition, the properties of the bio-active coating of the present invention can be varied easily, e.g., biostability, hydrophilicity etc. Also, the methods of synthesizing the present bio-active coatings are more efficient and take less time than previously disclosed methods. Another advantage of the present invention is that the reactions may be carried out at lower temperatures. Importantly, the reaction schemes of the present invention form fewer cross-links and provide higher polymer yields than previously described methods. Thus, these new coatings are well suited for application onto, for example, the luminal surface of a small caliber vascular graft.

The present invention contemplates coating implantable medical devices with bio-active coatings described herein. Any type of implantable device may be used with the present invention, such as, for example, vascular grafts. The bio-active coatings of the present invention have been formed to be particularly useful in several caliber grafts where patency is especially critical. Such grafts are advantageous because these bio-active coatings enable the grafts to function with significantly enhanced patency. Thus, these small caliber vascular grafts may be used in areas of the body where conventional sized grafts are contraindicated. As used herein, "small caliber" means an inner tube diameter of 5.0 mm or less. Such small caliber grafts are especially useful in cerebral or coronary blood vessel by-pass procedures.

Synthetic polymers used for vascular grafts include polyester, e.g. polyethylene terepthalate, polyurethane, and polytetrafluoroethylene, among others. The graft must have a blood contacting (luminal) surface which is considered to have hydrophobic character whereby the pendent group containing the hydrophobic spacer and bio-active agent are repelled away from the synthetic polymer surface by the natural repulsion forces between hydrophobic and hydrophilic groups. These natural repulsion forces make the bio-active agent more available for interaction with the blood and more efficient for carrying out such functions as enhancing antithrombogenicity and the like. Thus, although the coatings are intended to be particularly useful in small caliber ePTFE vascular grafts, use in both small and large sized grafts made of various polymers are contemplated.

Grafts formed of ePTFE have a fibrous structure which is defined by interspaced nodes interconnected by elongated fibrils. The spaces between the node surfaces that are spanned by the fibrils are defined as the internodal distance (IND). The art is replete with examples of vascular grafts made of microporous ePTFE tubes useful as vascular grafts. The porosity of an ePTF vascular graft is controlled by varying the IND of the nicroporous structure of the tube. An increase in the IND within a given structure results in enhanced tissue ingrowth, as well as cell endothelialization, along the inner surface thereof. This tissue ingrowth and endothelialization promotes stability, enhances radial strength and increases the patency of the graft. Thus, the presence of intact nodes and fibrils on ePTFE surfaces is critical for the long-term function of this substrate.

The node and fibril structure of the ePTFE grafts of the present invention remain intact even after plasma treatment. Thus, plasma treating the grafts of the present invention does not appear to substantially affect the physical structure of the ePTFE graft. Accordingly, plasma treatment would not be expected to reduce the long-term patency or ability of these grafts to support tissue ingrowth.

Once an ePTFE vascular graft is plasma primed, one or more coatings of the present invention may be applied thereto. It should be noted that the internodal space, e.g., the space between the nodes that is not spanned by fibrils, is substantially covered by such coatings. Also, the elongated fibrils are substantially covered by such coatings. In contrast, where there are no fibrils in the IND, no bio-active coating is observed. This absence of coating material allows for cell ingrowth to occur without interference from such coatings.

Thus, the micro-structure of the inner surface of an ePTFE graft remains intact following plasma treatment and application of one or more coatings of the present invention. In particular, plasma priming the inner substrate surface followed by application of one or more layers of the bio-active polymer coating described herein does not destroy the ePTFE nodes or cleave the fibrils. Thus, the present invention does not interfere with, and in fact, improves the patency of an ePTFE graft. Therefore, such a graft is useful where small diameter grafts of ePTFE are required and the patency of such a graft must be ensured.

In order to ensure that the bio-active coatings described herein remain secured to the inner surface of the ePTFE graft, these surfaces are primed with a hydrogen-rich plasma prior to application of the bio-active coating. Providing organic surface coatings on substrate materials by means of plasma polymerization, as stated above, is known. For a review-type publication in this area, see an article by H. Yasuda, *J. Macromol. Sci.-Chem.*, A10(3), pp. 383–420 (1976), entitled "Plasma for Modification of Polymers." According to Yasuda, plasma created by electric glow discharges contain a variety of species which are chemically active or energetic enough to cause chemical reactions, i.e., covalent bonding to a suitable substrate material.

As used herein, "plasma" is used in the sense of "low-temperature plasma" or "cold plasma" produced by glow discharges. Plasmas created by electric glow discharges contain a variety of species which are chemically active or energetic enough to cause chemical reactions, i.e., covalent bonding to a suitable substrate material. For example, electrons, ions of both charges, excited molecules at various levels of excitation, free radicals, and photons of various energies are created by cold plasma.

In a preferred embodiment, prior to deposition of the bio-active coating, the hydrophobic surface is treated with a hydrogen-rich plasma to provide better adhesion of the coating. This plasma treatment can be performed using conventional methods known in the art. For example, radio-frequency plasma polymer deposition of purified water vapor on untreated ePTFE tubes can be used. Purified water vapor is described but any hydrogen-rich material, such as, alcohols, diols, other polyhydroxy compounds, thiols, primary amines and secondary amines are useful. The ePTFE tubes are inserted into a glass vessel 75 cm in length and 10 cm in diameter, which is sealed. The vessel is evacuated by a mechanical pump, then back-filled with a hydrogen-rich gas, such as, for example, water vapor. The system pressure is monitored by a capacitance monometer connected to an adaptive pressure control system (AdapTorr™, a power supply model AC-2, controller model ACR-26, Vacuum General). Pressure is controlled by altering the position of an in-line adjustable butterfly valve. Brass capacitor rings are wrapped around the reactor and spaced 12 inches apart. The ePTFE tubes are placed anywhere in a 10-inch zone centered between the rings. A 13.56 MHZ RF generator (Tegal Corporation Novato, Calif.) is then turned on and a plasma formed. The gas flow rate is from about 1 ml/minute to about 500 ml/minute. The ePTFE tubes are etched with argon plasma (350 mtorr argon, 50 watts (W), 5 minutes) and then are treated with plasma for 10 minutes (water: 100 mtorr, 50 W) in the plasma reactor. Water vapor is continuously passed over the sample for one-half hour after the plasma reaction is terminated to quelch any active surface groups. First argon, then air is bled into the reactor until the system returns to atmospheric pressure. The reactor is then opened under a laminar flow hood and the ePTFE tubes are removed.

The plasma-primed ePTFE grafts are then dipped, sprayed, steeped or otherwise contacted with one of the bio-active coatings described hereinbelow. As used herein, "contacting" the article to be coated with a coating of the present invention refers to these and other conventional methods of applying such coatings to a substrate surface. In addition, multiple bio-active coatings of the present invention may be applied. One particular method of coating or impregnating a graft involves filling it with the bio-active coating and applying pressure to force the coating into the interstices of the graft. Pressure or force can be applied using a number of mechanical means. Once coated, the grafts are allowed to dry and then are subjected to sterilizing conditions prior to introduction into the body. Thus, the bio-active coatings of the present invention must be made of materials that can withstand such treatment and conditioning.

Accordingly, the polymer backbones of the present bio-active coatings are comb-type polymers in which bio-active molecules, such as heparin, are attached off of pendant groups. Preferred polymer backbones are siloxane-urethane copolymers, and most preferably, polyurethane and polyurethaneurea polymer backbones.

A composition of the invention was synthesized by reacting a polyol and a methyl diisocyanate to form a prepolymer. This prepolymer was reacted with a chain extender in the presence of a saturated carboxylic acid. Preferably, the chain extender is butanediol (BDO).

Preferably, the saturated carboxylic acid is

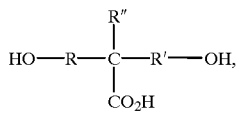

where R=alkyl of about 1 to about 10 carbon atoms; R'=alkyl of about 1 to about 10 carbon atoms; and R'=alkyl or aryl of about 1 to about 10 carbon atoms. Preferably, R=R'=$CH_2$ and R"=$CH_3$.

The resulting product was a polyurethane polymer containing carboxyl functionality (I). This polymer was then added to a hydrophilic amine-terminated poly(ethylene oxide), PEO, (II) in the presence of a dehydrating agent as indicated below:

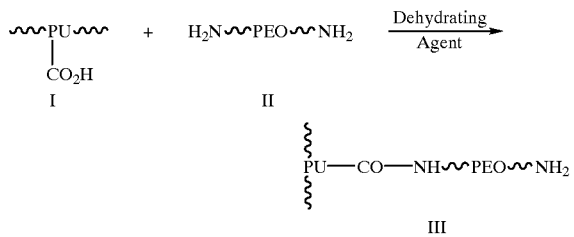

The product (III) of the reaction indicated above is a polymer-spacer complex characterized by an amide linkage between the spacer and the polymer and an amine group on the free terminal end of the spacer. A bio-active agent, such as heparin, is then covalently bound to the polymer-spacer complex in the presence of a dehydrating agent, such as 1-(3-dimethylaminopropyl)-3-ethylcarbodiimide (EDC), as indicated below:

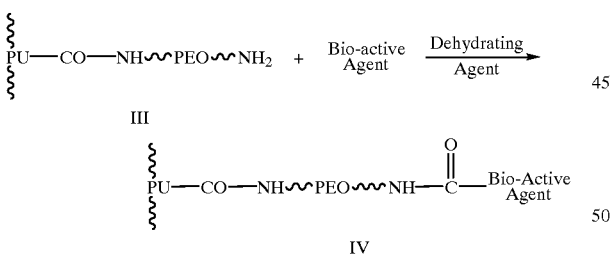

The product (IV) of the reaction indicated above is characterized by an amide linkage between the spacer and the bio-active molecule, e.g., heparin. Thus, in this embodiment, the reaction product IV is characterized by amide linkages between its respective units, i.e., between the polyurethane backbone and the spacer, and between the spacer and the bio-active agent. This composition and its method of synthesis will be referred to hereinafter as "Inventive Embodiment I."

In an another embodiment of this invention, a polyol and a methyl diisocyanate were reacted to form a prepolymer. This prepolymer was reacted with a chain extender in the presence of an unsaturated carboxylic acid. Preferably, the chain extender is BDO. Thus, in this embodiment, an unsaturated carboxylic acid is substituted for the saturated carboxylic of Inventive Embodiment I. Preferably the unsaturated carboxylic acid is

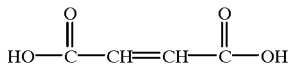

but others, such as any internally unsaturated alpha, omega-dicarboxylic acid (e.g., oleic acid or linoleic acid) are useful.

The resulting unsaturated polyurethane polymer containing carboxyl functionality was formed as illustrated below (V). This polymer was then added to a hydrophilic amine-terminated poly(ethylene oxide), PEO, (II) in the presence of a dehydrating agent as indicated below:

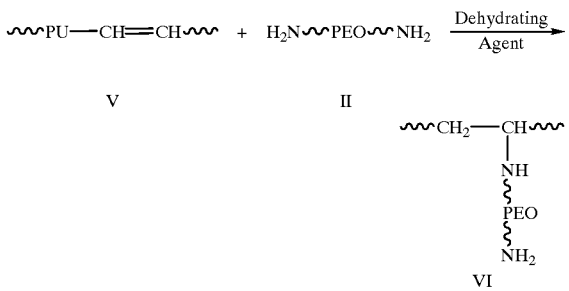

The product (VI) of the reaction indicated above is an unsaturated polymer-spacer complex characterized by an amine linkage between the spacer and the polymer. A bio-active agent then is grafted to the polymer-spacer complex in the presence of a dehydrating agent, such as, EDC as indicated below:

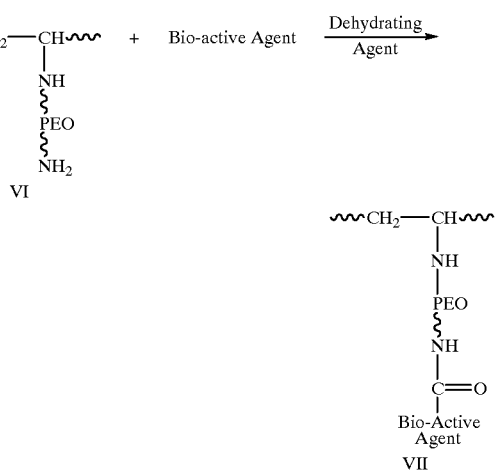

The product (VII) of the reaction indicated above is characterized by an amide linkage between the spacer and the bio-active molecule. Thus, in this embodiment, the reaction product VII is characterized by different linkages between its respective units, i.e., an amine linkage between the polyurethane backbone and the spacer and an amide linkage between the spacer and the bio-active agent. This composition and its method of synthesis will be referred to hereinafter as Inventive Embodiment II.

In Inventive Embodiments I and II, dehydrating agents are used to facilitate the reaction in which the spacer is covalently bound to the polyurethane backbone. Preferably, the chemical bond formed therebetween is either an amide or amine chemical linkage. Similarly, dehydrating agents are used to facilitate the reaction in which the bio-active agent is covalently bound to the polyurethane backbone via the hydrophilic amine-terminated spacer. In this reaction, the linkage between the spacer and the bio-active agent is always an amide. Preferably, EDC increases the rate of reaction by removing water; however other dehydrating agents, such as dicyclohexylcarbodiimide, may also be used.

As Table 1 indicates, the present invention, e.g., Inventive Embodiments I and II, significantly improves upon previously described bio-active coating compositions and methods of making same, such as the aforementioned Park Method described herein.

TABLE 1

|  | Park Method | Inventive Embodiment I | Inventive Embodiment II |
| --- | --- | --- | --- |
| Polymer Yield (gm/gm starting material) | 0.40 ± 0.5 | 1.05 ± 0.12 | 0.86 |
| Level of Polymer Cross-Linking | Moderate (1–60) | Negligible–Low (0–15) | Negligible–Low (0–25) |
| Factor Xa Heparin Activity µg/cm | 0.03–0.13 | 0.3–0.09 | 0.05 |

As illustrated in Table 1, the methods of the present invention provide for approximately a 100% increase in polymer yield while significantly decreasing the amount of polymer cross-linking, i.e. unwanted side-reactions and cross-sections, and without sacrificing heparin bio-activity. Thus, such coatings are particularly suited for use in small caliber vascular grafts where it is especially important to ensure the patency of these grafts.

The bio-active agent of the present invention is bound to the polymer backbone via a spacer group. The spacer group may include oxygenated polyolefins, aliphatic polyesters, polyamino acids, polyamines, hydrophilic polysiloxanes, hydrophilic polysilazanes, hydrophilic acrylates, hydrophilic methacrylates, linear and lightly branched polysaccharides. The length of the spacer, as further discussed herein, is useful in controlling and enhancing the availability of the bio-active agent, since the purpose of the spacer is to tether the bio-active agents such as heparin away from the polymer substrate surface. The spacer group is intended to be hydrophilic in order to take advantage of the natural repulsive forces of the hydrophobic substrate. The spacer group should have reactive functional groups on each end that are capable of reacting with and binding to the polymer backbone and bio-active agent respectively. Preferably, the spacer group has a hydrophilic functional group on each end, such as a carboxylic acid group or an amine group. An amino end-blocked poly(ethylene oxide), PEO, is a preferred example.

Hydrophilic poly(ethylene oxide) spacers are preferred because they have low interfacial free energy, lack binding sites, and exhibit highly dynamic motion. These characteristics are important because they increase the bioactivity of a PEO-linked bio-active agent, e.g., heparin. See, K. D. Park et al., supra.

The length of the spacer group may be used to control the bio-active agent's activity. It is known in the art that the anti-thrombogenic activity of heparin is increased when it is positioned a certain distance from the substrate to which it is bound. For example, the bioactivity of polymer-spacer-heparin coatings were evaluated as a function of spacer length (as measured by molecular weight) for four different commercially available spacers. A six carbon chain alkyl spacer, a PEO 200, a PEO 1000 and a PEO 4000 were used in this comparison. In this experiment, the polymer-PEO 4000-Heparin-coated surface maintained the highest bio-activity. See, K. D. Park et al., supra. Thus, methods are available in the art for controlling the activity of a polymer-bound bio-active agent. By utilizing such methods, one may determine the optimal length of the spacer. Accordingly, as used herein, "bio-effective distance" means the distance between the bound bio-active agent and the polymer backbone which corresponds to a desired level of activity in the bio-active agent.

Thus, in the present invention, control over the bio-active agent's activity is achieved by varying the length, e.g., molecular weight, of the spacer group. The spacer group may have a molecular weight of about 100 to about 200,000 daltons (approximately 9–400 atoms). Preferably, the spacer group has a molecular weight of about 200 to about 50,000 daltons. Most preferably, the spacer group has a molecular weight of about 1,000 to about 10,000 daltons. The best results are achieved, however, when the amino end-blocked poly(ethylene oxide) has a molecular weight of 4,000 daltons.

In addition to the molecular weight of the spacer, the natural repulsive forces between the hydrophobic surface of the medical device and the hydrophilic spacer helps to tether, or extend the bio-active molecule away from the surface. Thus, these natural repulsive forces also contribute to the increased patency of the grafts of the invention by maximizing the ability of the bio-active agent to interact with its physiological environment.

In accordance with the present invention, a significant reduction of thrombus formation and/or infection associated with the use of medical articles is achieved by combining an anti-thrombogenic and/or anti-infective agent in a coating to be applied to the host-contacting surface(s) of the article. A variety of anti-infective agents as known in the art may be used, including, antibiotics, such as penicillin and antibacterial agents such as silver sulfadiazine. Similarly, a variety of anti-thrombogenic agents known in the art may be used, including, heparin, prostaglandins, urokinase, streptokinase, sulfated polysaccharide, and albumin. In some cases it may be desirable to provide either dual anti-infective or anti-thrombogenic action with two or more agents. Additionally, it may be desirable to combine an anti-infective and an anti-thrombogenic action by combining two or more of these different agents. The invention will be described in terms of the preferred heparin, an anti-thrombogenic agent of known safety and high anti-coagulation activity, with the understanding that the invention contemplates any bio-active agent and specifically any anti-thrombogenic and/or anti-infective agent which may be grafted to the polymer backbone via the spacer by the method of the present invention.

An implantable medical device of the invention may be any medical article compatible with a polymer bound bio-active agent coating which, absent the coating, may lead to thrombus formation and/or infection when in contact with a body tissue or fluid. Exemplary of, but not limited to, such devices are vascular access (arterial and venous) catheters, introducers, vascular grafts, urinary catheters and associated articles, such as drainage bags and connectors, and all abdominal cavity drainage tubing, bags and connectors. Thus, in most cases, these devices will contact body fluids, such as, blood, urine, etc., however, the present invention is not limited to such conditions.

Surface-modified implantable sheet materials are also contemplated by the present invention. Such materials may be manufactured in sheets, layers, lamina, leafs, membranes, films, coatings and the like so that they may be custom fitted to various applications. Examples include, without limitation, surgical mesh, surgical patches, hernia plugs and the like. In accordance with the methods provided herein, such materials may be plasma-primed and then coated with any of the bio-active coatings of the present invention. Thus, commercial quantities of such sheets can be generated for use in a number of different applications.

Various shapes and surface characteristics of the polymer substrate as determined by the specific circumstances may also be used in the present invention. Preferred devices are polymeric, most preferably expandable polytetrafluoroethylene (ePTFE) small caliber vascular grafts.

It is contemplated that at least one surface of an implantable medical device be coated by the bio-active coating of the present invention. Multiple surfaces of the medical device, however may be so coated depending on the intended use.

Certain substrates, such as ePTFE, require plasma treatment with a hydrogen-rich plasma prior to application of the bio-active coating. As previously mentioned, conventional plasma techniques may be employed. Application of the bio-active coating can be performed by dipping, spraying or other techniques. It is preferred that from about 1 to about 10 coatings of the bio-active coating be used. The number of coatings to be used, however, will depend on the substrate surface to be coated and the requirements of the particular situation. Thus, in one embodiment of the present invention, the luminal surface of a small caliber ePTFE vascular graft is first treated with a hydrogen-rich plasma followed by application of one or more coats of a bio-active coating described herein.

In a further embodiment, the present invention includes a biocompatible backbone polymer having carboxyl functionality or unsaturated functionality, an amine-terminated spacer and a bio-active agent. In this embodiment, a dehydrating agent, such as, 1-(3-dimethylaminopropyl)-3-ethyl carbodiimide, may be used to facilitate binding of the polymer backbone to one end of the amine terminated spacer and of the bio-active agent to the other non-reacted end of the spacer.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of imparting a bio-active coating to a surface of an article which comprises:

a) plasma treating said surface with a gaseous material in an ionization chamber whereby hydrophilic groups generated from said gaseous material are introduced onto said surface to provide a hydrophilic environment thereon, and b) contacting said surface with a polymer bound bio-active composition represented by the structure:

wherein P is a bio-compatible polymer, $R^1$ is —NH:$R^2$ is a hydrophilic amine-terminated spacer and $R^3$ is a bio-active agent.

2. The method of claim 1, wherein the bio-compatible polymer is selected from the group consisting of bio-compatible polymers having carboxyl functionality, unsaturated functionality, and mixtures thereof.

3. The method of claim 1, wherein the spacer is selected from the group consisting of oxygenated polyolefins. aliphatic polyesters, polyamino acids, polyamines, hydrophilic polysiloxanes, hydrophilic polysilazanes, hydrophilic acrylates, hydrophilic methacrylates, linear and lightly branched polysaccharides.

4. The method of claim 1, wherein the bio-active agent is selected from the group consisting of anti-thrombogenic agents, antibiotic agents, antibacterial agents, their pharmaceutical salts, and mixtures thereof.

* * * * *